(12) United States Patent
Richter et al.

(10) Patent No.: US 6,914,162 B2
(45) Date of Patent: Jul. 5, 2005

(54) METHOD FOR PRODUCING HYDROFORMYLATION PRODUCTS OF OLEFINS WITH 2 TO 8 CARBON ATOMS

(75) Inventors: Wolfgang Richter, Wachenheim (DE); Roland Krokoszinski, Weisenheim a.Berg (DE); Rolf Müller, Dannstadt-Schauernheim (DE); Bernhard Geissler, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 10 days.

(21) Appl. No.: 10/312,365
(22) PCT Filed: Jun. 27, 2001
(86) PCT No.: PCT/EP01/07343
§ 371 (c)(1), (2), (4) Date: Dec. 26, 2002
(87) PCT Pub. No.: WO02/02496
PCT Pub. Date: Jan. 10, 2002

(65) Prior Publication Data

US 2004/0024259 A1 Feb. 5, 2004

(30) Foreign Application Priority Data

Jun. 28, 2000 (DE) ......................................... 100 31 517

(51) Int. Cl.[7] .............................................. C07C 45/50
(52) U.S. Cl. ........................ 568/451; 568/454; 568/475
(58) Field of Search .............................. 568/451, 454, 568/475

(56) References Cited

U.S. PATENT DOCUMENTS

| | | | |
|---|---|---|---|
| 2,846,464 A | 8/1958 | Brodkey et al. | 260/475 |
| 4,711,968 A | 12/1987 | Oswald et al. | 568/454 |
| 4,778,929 A | 10/1988 | Zehner et al. | 568/454 |
| 2003/0153791 A1 | 8/2003 | Richter et al. | |
| 2003/0176743 A1 | 9/2003 | Walz et al. | |
| 2004/0015011 A1 | 1/2004 | Krokoszinski et al. | |

FOREIGN PATENT DOCUMENTS

| | | | |
|---|---|---|---|
| EP | 648 730 | | 4/1995 |
| GB | 2055367 | * | 3/1981 |

* cited by examiner

Primary Examiner—Johann Richter
Assistant Examiner—Sikarl A. Witherspoon
(74) Attorney, Agent, or Firm—Novak Druce & Quigg, LLP

(57) ABSTRACT

A process for preparing hydroformylation products of olefins having from 2 to 8 carbon atoms comprises a) feeding a hydrocarbon feedstock into a cracking/dehydrogenation zone and subjecting it to thermal and/or catalytic cracking and/or dehydrogenation to give an olefin-containing cracker gas, b) subjecting the cracker gas or fractions thereof to a fractionation to give at least one $C_i$-olefin-enriched hydrocarbon stream and at least one $C_i$-olefin-depleted hydrocarbon stream, c) feeding the $C_i$-olefin-enriched hydrocarbon stream together with carbon monoxide and hydrogen into a hydroformylation zone and reacting it in the presence of a hydroformylation catalyst, d) separating a stream consisting essentially of unreacted $C_i$-olefin and saturated $C_i$-hydrocarbon from the output from the hydroformylation zone, e) recirculating at least part of the stream consisting essentially of unreacted $C_i$-olefin and saturated $C_i$-hydrocarbon to step b), where i is an integer from to 8.

The proposed coupling of the hydroformylation with, for example, a steam cracker allows complete hydroformylation of the olefins produced without olefin losses via the waste gas.

7 Claims, 1 Drawing Sheet

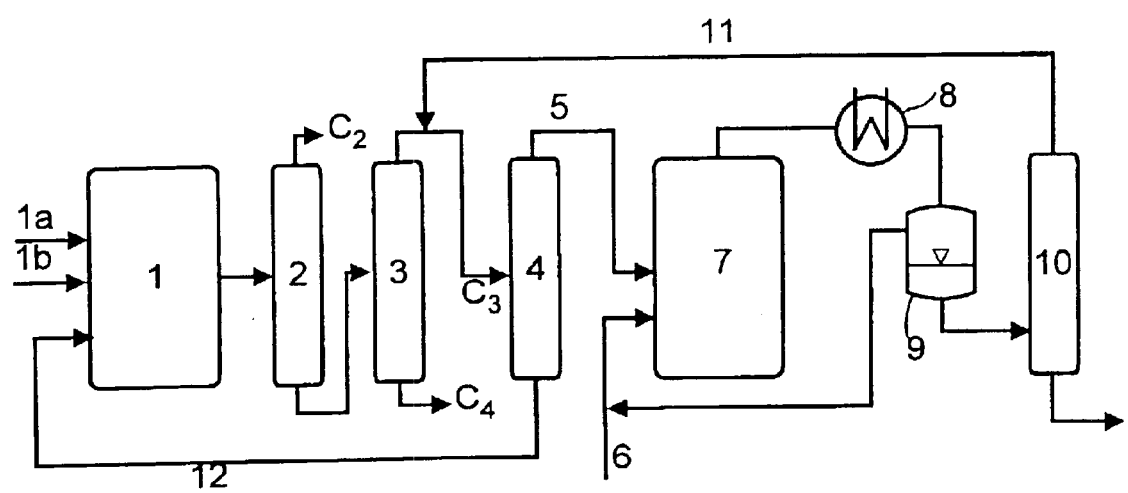

METHOD FOR PRODUCING HYDROFORMYLATION PRODUCTS OF OLEFINS WITH 2 TO 8 CARBON ATOMS

The present invention relates to a process for preparing hydroformylation products of olefins having from 2 to 8 carbon atoms.

Hydroformylation or the oxo process is an important industrial process for preparing aldehydes from olefins, carbon monoxide and hydrogen. These aldehydes can, if desired, be hydrogenated by means of hydrogen to form the corresponding alcohols either in the same process step or subsequently in a separate hydrogenation step. Hydroformylation is carried out in the presence of catalysts which are homogeneously dissolved in the reaction medium. Catalysts used are generally compounds or complexes of metals of transition group VIII, especially Co, Rh, Ir, Pd, Pt or Ru compounds or complexes which may be unmodified or modified with, for example, amine- or phosphine-containing compounds.

The output from the hydroformylation reactor comprises the hydroformylation product and generally also unreacted olefin. The latter is separated from the hydroformylation product and returned together with fresh carbon monoxide and hydrogen to the hydroformylation reactor. However, the inert components introduced with the olefin or formed by secondary reactions, e.g. saturated hydrocarbons which are not capable of hydroformylation, are also recirculated to the reactor together with the recirculated olefin. To prevent the concentration of the inert components rising continuously in the hydroformylation reactor and reaching values at which the hydroformylation reaction ceases, a substream of the recirculated olefin has to be bled continuously from the process in order to remove the inert components from the system.

However, the bleed stream consists only partly of inert components. A significant proportion is formed by unreacted olefin which is thus lost to the reaction. To keep the bleed stream and the losses associated therewith small, an olefin feed of high purity is generally used.

Although it is technically possible to separate the saturated hydrocarbon from the bleed stream and to recirculate only the unreacted olefin or an olefin-enriched stream to the reaction zone, the separation of olefins and saturated hydrocarbons having the same number of carbon atoms requires complicated apparatuses which are associated with a considerable capital cost.

EP-A 0 648 730 discloses a process for preparing an oxo product obtained from propylene, in which a gas stream comprising unreacted propylene and propane is separated from the product stream from a propylene hydroformylation. Selective adsorption of propylene on an adsorbent and subsequent desorption gives a propylene-enriched gas stream which is at least partly recirculated to the reaction zone. The alternating adsorption and desorption cycles require periodic pressure and/or temperature changes. The apparatuses required for this are complicated and susceptible to malfunctions.

Olefins such as ethylene, propylene and butenes are produced on a large scale by thermal and/or catalytic cracking and/or dehydrogenation of a hydrocarbon feedstock such as naphtha, natural gas, isobutane, etc. The individual olefins are isolated in the desired purity from the crude cracking products.

It is an object of the present invention to provide an integrated process for the preparation and hydroformylation of olefins, in which costly plants for the separation of olefins and saturated hydrocarbons are utilized optimally.

We have found that this object is achieved by a process for the hydroformylation of olefins having from 2 to 8 carbon atoms, which comprises
a) feeding a hydrocarbon feedstock into a cracking/dehydrogenation zone and subjecting it to thermal and/or catalytic cracking and/or dehydrogenation to give an olefin-containing cracker gas,
b) subjecting the cracker gas or fractions thereof to a fractionation to give at least one $C_i$-olefin-enriched hydrocarbon stream and at least one $C_i$-olefin-depleted hydrocarbon stream,
c) feeding the $C_i$-olefin-enriched hydrocarbon stream together with carbon monoxide and hydrogen into a hydroformylation zone and reacting it in the presence of a hydroformylation catalyst,
d) separating a stream consisting essentially of unreacted $C_i$-olefin and saturated $C_i$-hydrocarbon from the output from the hydroformylation zone,
e) recirculating at least part of the stream consisting essentially of unreacted $C_i$-olefin and saturated $C_i$-hydrocarbon to step b), where i is an integer from 2 to 8.

In general, at least part of the $C_i$-olefin-depleted hydrocarbon stream is recirculated to the cracking/dehydrogenation zone. Thermal cracking is preferably carried out in the presence of water vapor.

The process of the present invention comprises the steps of preparation of an olefin-containing cracker gas from a hydrocarbon feedstock (e.g. in a steam cracker or a hydrocarbon dehydrogenation plant), fractionation of the cracker gas to give a fraction enriched in an individual olefin and hydroformylation of this fraction. The stream of $C_i$-olefin-enriched hydrocarbon obtained in step b) can also be divided and only part of it be hydroformylated. An important feature of the invention is that a stream which consists essentially of unreacted olefin and saturated hydrocarbon having the same number of carbon atoms and has been separated off from the output from the hydroformylation is returned directly to the fractionation step for the olefin-containing cracker gas and is fractionated together with the cracker gas or fractions thereof. The joint operation of the isolation of olefin from the cracker gas and the selective recirculation of unreacted olefin to the hydroformylation requires construction of only one separation plant. Since plants for the separation of olefins and saturated hydrocarbons are very complicated, this is associated with a significant capital cost saving. In the present description, the term "cracker gas" is used for any reaction product comprising olefins and saturated hydrocarbons regardless of whether it is obtained by cracking or by dehydrogenation.

Suitable hydrocarbon feedstocks for the process of the present invention are, for example, naphtha, natural gas or fractions thereof, propane, isobutane or other hydrocarbon streams obtained, for example, in industrial processes as by-product streams or waste streams.

The cracker gas obtained by cracking/dehydrogenation generally comprises a mixture of olefins and saturated hydrocarbons which can, particularly in the case of cracker gas obtained by cracking, have different numbers of carbon atoms. The cracker gas is subjected to a fractionation to give at least one $C_i$-olefin-enriched hydrocarbon stream and at least one $C_i$-olefin-depleted hydrocarbon stream. If hydrocarbons having different numbers of carbon atoms are present in the cracker gas, a $C_i$-hydrocarbon fraction is, in general, firstly isolated from the mixture and is then fractionated further to give an olefin-enriched stream and an olefin-depleted stream. Thus, in the fractionation of cracker gas obtained by steam cracking of naphtha, a $C_2$-hydrocarbon fraction and a $C_3$-hydrocarbon fraction are obtained first and are then in turn fractionated further to give ethylene and ethane or propylene and propane. The fractionation generally comprises at least one rectification step.

The index i is an integer from 2 to 8, preferably from 2 to 4, in particular 3. The process of the present invention can be used to prepare, in particular, the hydroformylation products of ethylene, propylene, 1-butene and/or 2-butene, with particular preference being given to propylene.

The process of the present invention can be implemented, for example, in an existing process for the hydroformylation of propylene obtained by cracking of naphtha in a steam cracker, by passing a stream which consists essentially of unreacted propylene and propane and has been separated off from the output from the hydroformylation zone directly into the $C_3$ column of the steam cracker (see below).

It is also possible, for example, to feed a propylene-containing stream which has been obtained by dehydrogenation of propane and may still contain, for example, from 0.5 to 40% by weight of propane into the hydroformylation zone and to recirculate the stream consisting essentially of unreacted propylene and propane which has been separated off from the output from the hydroformylation zone to the work-up section of the propane dehydrogenation plant; the propylene-depleted stream obtained in this way is advantageously recirculated as feedstock to the dehydrogenation zone.

The $C_i$-olefin-enriched hydrocarbon stream generally comprises at least 60% by weight, preferably at least 70% by weight, in particular at least 90% by weight, e.g. from 90 to 97% by weight, of $C_i$-olefin, with the balance consisting essentially of saturated $C_i$-hydrocarbon. The $C_i$-olefin-depleted hydrocarbon stream generally contains less than 15% by weight, usually less than 5% by weight, of $C_i$-olefin, with the major part being saturated $C_i$-hydrocarbon.

The individual steps of the process of the present invention are known per se and their specific form is not subject matter of the invention. They are illustrated in the following by means of advantageous or preferred embodiments.

Thermal cracking is a free-radical dissociation of hydrocarbons which is usually carried out under pressure and commences at from about 400 to 500° C. Thermal cracking commences with the homolysis of a C—C bond to form two free radicals. Both alkyl radicals can then abstract a hydrogen atom from a further hydrocarbon molecule and thus generate a new free radical and a shorter-chain alkane. Both original free radicals or the newly generated free radical can undergo β-cleavage to form an olefin molecule and a shorter-chain alkyl radical. The events during cracking thus involve changes in the $H_2$ content and in the carbon skeleton. The production of low molecular weight olefins is favored if thermal cracking is carried out at high temperature, a short residence time and a low partial pressure. To reduce the partial pressure of the hydrocarbons, an additional gas, usually steam, is mixed into the hydrocarbon feedstock to be pyrolyzed ("steam cracking").

Purely for the purposes of illustration, the procedure for the cracking of naphtha can be divided into the following individual steps:

(1) cracking of naphtha in multitube furnaces,
(2) quenching of the cracker gas,
(3) compression and purification of the cracker gas and
(4) drying, cooling and low-temperature distillation.

After prevaporization using superheated steam, naphtha is introduced into the, for example, 50-200 m long and 80-120 mm wide tubes of the cracking furnace. Modern high-severity cracking furnaces generally have vertical chromium-nickel tubes. They are heated directly by combustion of fuel gases or oils to about 1050° C. at the hottest point. In the ACR process, temperatures of up to 2000° C. and pressures of 3.5 bar are reached in a ceramic-lined reactor.

The cracking products leave the cracking section at high temperature and have to be quenched quickly to about 300° C. to avoid subsequent reactions. This is achieved initially indirectly with steam generation in quench coolers and subsequently by spraying quenching oil into the gas. Process water and pyrolysis gasoline are subsequently separated off and the gaseous constituents are compressed and purified. To remove $H_2S$ and $CO_2$, an alkaline scrub, e.g. using from 5 to 15% strength sodium hydroxide solution, is generally employed.

Before the actual work-up, careful drying has to be carried out so that the subsequent low-temperature distillation is not adversely affected by ice formation. The dried crude gas is then cooled in a number of stages and subjected to fractional distillation in a system of columns.

In a typical intermediate-pressure low-temperature process, the dried cracker gas is cooled to from −35° C. to −45° C. and fed into the methane column which is maintained at a temperature of about −90° C. at the top. The bottom product from the column, which comprises the $C_2$- and higher hydrocarbons, is passed to a further column in which the total $C_2$ fraction is taken off at the top, so that the bottom product consists essentially of $C_3$- and higher hydrocarbons. The product taken off at the top of the column is conveyed through a cooler and into the ethylene column. Pure ethylene is taken off at the top of the ethylene column, and the bottom product, essentially ethane, is generally recirculated to the cracking furnace. The bottom product comprising $C_3$- and higher hydrocarbons obtained after separating off the $C_2$ fraction is introduced into a further column for further fractionation. The $C_3$ fraction which goes over at the top of this column is, optionally after selective hydrogenation of the propyne and allene present, fractionated in the $C_3$ column to give propylene and propane. Propylene can be isolated in a desired purity of up to 99.9%

Alternatively, olefins can be prepared by dehydrogenation of suitable hydrocarbon feedstocks essentially without cleavage of C—C bonds. Possibilities are, in particular, the dehydrogenation of propane to propylene and of butane to butenes. The dehydrogenation is generally carried out using catalysts. A suitable catalyst is, for example, chromium oxide on activated alumina as support, optionally with additives such as $K_2O$, $CeO_2$, $SiO_2$, $TiO_2$, $ZrO_2$, $P_2O_5$, etc. Other possible catalysts are catalysts based on calcium-nickel phosphate.

The dehydrogenation unit generally comprises one or more reactors charged with catalyst, e.g. fluidized-bed reactors. The mixture of fresh and, if desired, recirculated hydrocarbon feedstock is preheated and flows into the reactor. The reaction gas is cooled and compressed; products of value can be recovered from the uncondensable fraction by scrubbing with suitable solvents. The liquefied fraction can be separated into a $C_i$-olefin-enriched stream and a $C_i$-olefin-depleted stream by, for example, fractional distillation.

The $C_i$-olefin-enriched hydrocarbon stream is fed together with carbon monoxide and hydrogen into a hydroformylation zone.

Carbon monoxide and hydrogen are usually used in the form of a mixture, known as synthesis gas. The composition of the synthesis gas used in the process of the present invention can vary within a wide range. The molar ratio of carbon monoxide to hydrogen is generally from 2:1 to 1:2, in particular from about 45:55 to 50:50.

The temperature in the hydroformylation reaction is generally in a range from about 50 to 200° C., preferably from about 60 to 190° C., in particular from about 90 to 190° C. The reaction is preferably carried out at a pressure in the range from about 10 to 700 bar, preferably from 15 to 200 bar, in particular from 15 to 60 bar. The reaction pressure can be varied as a function of the activity of the hydroformylation catalyst used.

Suitable pressure-rated reaction apparatuses for hydroformylation are known to those skilled in the art. They include generally customary reactors for gas-liquid reactions, e.g. gas circulation reactors, bubble columns etc., which may be subdivided by internals.

Suitable hydroformylation catalysts are the customary transition metal compounds and complexes known to those skilled in the art, which can be used both with and without cocatalysts. The transition metal is preferably a metal of transition group VIII of the Periodic Table, in particular Co, Ru, Rh, Pd, Pt, Os or Ir, especially Rh, Co, Ir or Ru.

Examples of suitable complexes are the carbonyl compounds of the abovementioned metals and also complexes whose ligands are selected from among amines, arylphosphines, alkylphosphines, arylalkylphosphines, olefins, dienes, etc., and mixtures thereof.

Specific examples of suitable complexes are rhodium complexes of the formula $RhX_m L^1 L^2 (L^3)_n$, where X is halide, preferably chloride or bromide, alkylcarboxylate or arylcarboxylate, acetylacetonate, arylsulfonate or alkylsulfonate, in particular phenylsulfonate and toluenesulfonate, hydride or the diphenyltriazine anion, $L^1$, $L^2$, $L^3$ are, independently of one another, CO, olefins, cycloolefins, preferably cyclooctadiene (COD), dibenzophosphole, benzonitrile, $PR_3$ or $R_2P\text{-}A\text{-}PR_2$, m is 1 or 3 and n is 0, 1 or 2. R (which may be identical or different) are alkyl, cycloalkyl and aryl radicals, preferably phenyl, p-tolyl, m-tolyl, p-ethylphenyl, p-cumyl, p-t-butylphenyl, p-$C_1$-$C_4$-alkoxyphenyl, preferably p-anisyl, xylyl, mesityl, p-hydroxyphenyl which may also be in ethoxylated form, sulfophenyl, isopropyl, $C_1$-$C_4$-alkoxy, cyclopentyl or cyclohexyl. A is 1,2-ethylene or 1,3-propylene. $L^1$, $L^2$ and $L^3$ are preferably each, independently of one another CO, COD, P(phenyl)$_3$, P(i-propyl)$_3$, P(anisyl)$_3$, P(OC$_2$H$_5$)$_3$, P(cyclohexyl)$_3$, dibenzophosphol or benzonitrile.

X is preferably hydride, chloride, bromide, acetate, tosylate, acetylacetonate or the diphenyltriazine anion, in particular hydride, chloride or acetate.

Preferred hydroformylation catalysts are phosphorus-containing rhodium catalysts such as RhH(CO)$_2$(PPh$_3$)$_2$ or RhH(CO)(PPh$_3$)$_3$.

Suitable hydroformylation catalysts are described, for example, in Beller et al., Journal of Molecular Catalysis A, 104 (1995), pp. 17–85, which is hereby fully incorporated by reference.

In the reaction zone, only partial conversion of the olefin fed in takes place per pass. The conversion is generally from 10 to 90%, based on the olefin fed in.

The output from the reaction zone is subjected to a single-stage or multistage separation operation to give at least a stream comprising the major part of the hydroformylation product and a stream consisting essentially of unreacted olefin and saturated hydrocarbon. Depending on the discharge method, further streams such as waste gases comprising synthesis gas and streams comprising high-boiling by-products of the hydroformylation and/or hydroformylation catalyst may be obtained and these are, optionally after work-up, recirculated wholly or in part to the reaction zone or discharged from the process. For example, the hydroformylation product and any components having a boiling point higher than that of the formylation product can firstly be separated from the output from the reaction zone. A mixture of unreacted olefin and saturated hydrocarbon can subsequently be condensed out.

However, the stream consisting essentially of unreacted olefin and saturated hydrocarbon is advantageously obtained by firstly separating a crude hydroformylation product comprising unreacted olefin and saturated hydrocarbon in dissolved form from the output from the reaction zone and then subjecting the crude hydroformylation product to a degassing step to give a stream consisting essentially of unreacted olefin and saturated hydrocarbon. The reactor output which has been freed of crude hydroformylation product is generally recirculated wholly or in part to the reaction zone. To degas the crude hydroformylation product, it can be depressurized, heated and/or treated with a stripping gas such as synthesis gas or nitrogen. Degassing is advantageously carried out in a column where the crude hydroformylation product is introduced in the middle region of the column, the degassed hydroformylation product is taken off at the bottom of the column and passed to further work-up, and a liquid or gaseous stream consisting essentially of unreacted olefin and saturated hydrocarbon is taken off at the top of the column.

The separation of the crude hydroformylation product from the output from the reaction zone can be carried out in various ways. For example, it is possible to use the liquid discharge process in which the output from the reaction zone, which is essentially liquid except for the synthesis gas used in excess for the hydroformylation, is depressurized and, as a result of the decrease in pressure, separated into a liquid phase consisting essentially of high-boiling by-products, the homogeneously dissolved hydroformylation catalyst and small amounts of hydroformylation product, unreacted olefin and saturated hydrocarbon and a gas phase consisting essentially of hydroformylation product, unreacted olefin and saturated hydrocarbon together with unreacted synthesis gas. The liquid phase can be returned as recycled stream to the reactor. The crude hydroformylation product is obtained by at least partial condensation of the gas phase. The gas phase which remains in the condensation is wholly or partly recirculated to the reaction zone.

The gas phase and liquid phase initially obtained in the depressurization step can advantageously be worked up by the method described in WO 97/07086. For this purpose, the liquid phase is heated and introduced into the upper region of a column, while the gas phase is introduced at the bottom of the column. Liquid phase and gas phase thus pass through the column in countercurrent. To increase contact of the phases with one another, the column is preferably provided with packing. As a result of the intimate contact of the gas phase with the liquid phase, the residual amounts of hydroformylation product, unreacted olefin and saturated hydrocarbon present in the liquid phase are transferred to the gas phase, so that the gas stream leaving the top of the column is enriched in hydroformylation product, unreacted olefin and saturated hydrocarbon compared to the gas stream introduced at the lower end of the column. The further work-up of the gas stream leaving the column and the liquid phase leaving the column is carried out in a customary manner, for example as described above.

Alternatively, it is possible to employ the gas recycle process in which a gas stream is taken off from the gas space of the hydroformylation reactor. This gas stream consists essentially of synthesis gas, unreacted olefin and saturated hydrocarbon together with an amount which depends on the vapor pressure in the hydroformylation reactor of the hydroformylation product formed in the hydroformylation reaction. The hydroformylation product is condensed out of the gas stream, e.g. by cooling, and the gas stream which has been freed of the liquid fraction is recirculated to the hydroformylation reactor.

The stream consisting essentially of unreacted olefin and saturated hydrocarbon comprises, for example, from 50 to 95% by weight, preferably from 60 to 80% by weight, of olefin and from 5 to 50% by weight, preferably from 20 to 40% by weight, of saturated hydrocarbon.

FIG. 1 schematically shows a plant for preparing hydroformylation products of propylene in which the process of the present invention can be carried out. Self-evident plant details which are not necessary for an understanding of the present invention have been left out. Prevaporized naphtha and superheated steam are introduced via lines (1a) and (1b) into a multitube furnace (1). The cracking products are, after quenching and drying, fed into a separation column (2) in which the entire $C_2$ fraction is taken off at the top. The bottom product from the column (2), which consists essentially of $C_3$- and higher hydrocarbons, is introduced into a column (3) for further fractionation. A $C_3$ fraction is taken off at the top and is fractionated in the $C_3$ column (4) to give a propylene stream (5) at the top and a propane stream at the bottom. The propane stream is recirculated via line (12) to the cracking furnace. The propylene stream (5) is fed to a hydroformylation reactor (7) to which synthesis gas is also fed via line (6). The propylene is reacted in the hydroformylation reactor to form butyraldehyde. A gas stream is taken from the gas space of the hydroformylation reactor (7), cooled in the cooler (8) and introduced into a phase separation vessel (9). The gaseous fraction from the phase separation vessel (9), which consists essentially of unreacted synthesis gas, unreacted propylene and propane, is recirculated to the hydroformylation reactor. The liquid fraction from the phase butyraldehyde together with propylene and propane dissolved therein, is fed into a degassing column (10) at the bottom of which largely gas-free butyraldehyde is obtained. The mixture of propylene and propane obtained at the top of the degassing column (10) is combined with the stream from the top of the column (3) and the combined stream is then fed into the $C_3$ column (4) of the steam cracker.

The invention is illustrated by the following example.

EXAMPLE

A plant as shown in FIG. 1 was employed. A feed stream of 10 t/h of "chemical grade propylene" (95% by weight of propylene and 5% by weight of propane) obtained at the top of the $C_3$ column (4) of a steam cracker and also the synthesis gas necessary for the reaction were fed into the hydroformylation reactor (7). The product formed, namely a mixture of n-butyraldehyde and isobutyraldehyde, together with the unreacted propylene and the propane introduced and formed in the reaction were discharged from the reactor with the aid of a circulating gas stream. The condensable components were condensed in the cooler (8) and collected in the separator (9). The liquid phase comprised 78.3% by weight of butyraldehyde, 14.3% by weight of propylene and 7.4% by weight of propane. It was fed (20.3 t/h) to the degassing column (10) where it was separated in a $C_3$-free aldehyde stream at the bottom (15.9 t/h) and a mixture of 66% by weight of propylene and 34% by weight of propane at the top (4.4 t/h).

This mixture was combined with the feed stream to the $C_3$ separation column (4) of the steam cracker, the latter being taken off from the top of the upstream $C_3/C_4$ separation column (3). In the $C_3$ separation column (4), the mixture was separated into a virtually propylene-free propane stream at the bottom and a mixture of 95% by weight of propylene and 5% by weight of propane at the top. The propylene/propane stream coming from the degassing column (10) had a proportion of 3.1 t/h of top product and of 1.3 t/h of bottoms from the $C_3$ separation column.

The virtually propylene-free propane stream from the bottom of the $C_3$ separation column (4) was recirculated as feedstock to the furnace of the cracker.

We claim:

1. A process for preparing hydroformylation products of olefins having from 2 to 8 carbon atoms, which comprises
   a) feeding a hydrocarbon feedstock into a cracking/dehydrogenation zone and subjecting it to thermal and/or catalytic crackinq and/or dehydrogenation to give an olefin-containing cracker gas,
   b) subjecting the cracker gas or fractions thereof to a fractionation to give at least one $C_i$-olefin-enriched hydrocarbon stream and at least one $C_i$-olefin-depleted hydrocarbon stream,
   c) feeding the $C_i$-olefin-enriched hydrocarbon stream together with carbon monoxide and hydrogen into a hydroformylation zone and reacting it in the presence of a hydroformylation catalyst,
   d) separating a stream consisting essentially of unreacted $C_i$-olefin and saturated $C_i$-hydrocarbon front the output from the hydroformylation zone,
   e) recirculating at least part of the stream consisting essentially of unreacted $C_i$-olefin and saturated $C_i$-hydrocarbon to step b), where i is an integer from 2 to 8.

2. A process as claimed in claim 1, wherein at least part of the $C_i$-olefin-depleted hydrocarbon stream is recirculated to the cracking/dehydrogenation zone.

3. A process as claimed in claim 1, wherein the fractionation in step b) comprises at least one rectification step.

4. A process as claimed in claim 1, wherein the $C_i$-olefin is propylene.

5. A process as claimed in claim 1, wherein the stream consisting essentially of unreacted $C_i$-olefin and saturated $C_i$-hydrocarbon is obtained by firstly isolating a crude hydroformylation product in which unreacted $C_i$-olefin and saturated $C_i$-hydrocarbon are present in dissolved form from the output from the hydroformylation zone and subjecting this crude hydroformylation product to a degassing step.

6. A process as claimed in claim 1, wherein the hydrocarbon feedstock is naphtha or natural gas or fractions thereof.

7. A process as claimed in claim 1, wherein thermal cracking is carried out in the presence of water vapor.

* * * * *